United States Patent [19]

Jarreau et al.

[11] Patent Number: 4,552,868

[45] Date of Patent: Nov. 12, 1985

[54] 14-AMINO STEROID DERIVATIVES, A PROCESS FOR THE PREPARATION THEREOF AND METHOD OF USE THEREOF

[75] Inventors: Francois-Xavier Jarreau, Versailles; Jean-Jacques Koenig, Vernou la Celle, both of France

[73] Assignee: Etablissements Nativelle S.A., Paris, France

[21] Appl. No.: 524,500

[22] Filed: Aug. 18, 1983

[30] Foreign Application Priority Data

Aug. 20, 1982 [FR] France .................................. 82 14425
Jun. 20, 1983 [FR] France .................................. 83 10130

[51] Int. Cl.[4] ............................................. A61K 31/70
[52] U.S. Cl. ......................................... 514/26; 536/5; 260/397.4
[58] Field of Search ............................ 536/5; 514/26; 260/397.5; 424/180

[56] References Cited

U.S. PATENT DOCUMENTS 4,331,802 5/1982 Wiesner et al. ........................ 536/5
4,402,948 9/1983 Matsumura et al. .................... 536/5

OTHER PUBLICATIONS

CA-86 (17): Par. 121616q, Abstract of an article by Astier et al., Bull. Soc. Chim. Fr. (1976) pp. 1581-1582.

*Primary Examiner*—Elbert L. Roberts
*Attorney, Agent, or Firm*—Sughrue, Mion, Zinn, Macpeak and Seas

[57] ABSTRACT

The invention relates to 14-amino steroid derivatives of formula (I):

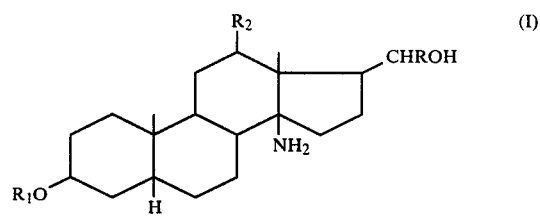

wherein R represents a hydrogen atom or a lower alkyl group with 1 to 4 carbon atoms, $R_1$ represents a substituted or unsubstituted sugar residue, and $R_2$ represents a hydrogen atom, a hydroxyl group or an $-OR_3$ group, wherein $R_3$ is a substituted or unsubstituted sugar residue; and acid salts thereof useful in the treatment of cardiac incapacity.

16 Claims, No Drawings

14-AMINO STEROID DERIVATIVES, A PROCESS FOR THE PREPARATION THEREOF AND METHOD OF USE THEREOF

FIELD OF THE INVENTION

The present invention, which was made in the CERES Laboratories—European Center for Scientific Research—relates to new steroid derivatives, and in particular to new 14-amino steroid derivatives substituted at the 3-position with a sugar derivative, a process for their preparation and a method for their use in therapy.

BACKGROUND OF THE INVENTION

French Patent Application 2,464,270 describes 14-amino steroid type compounds, and in particular hydroxylated derivatives of 14-amino androstane and 14-amino 21-nor pregnane.

In addition, steroid alkaloids of pregnane and androstane substituted at the 14-position by an amino group are well known, for example 14β-amino 3β,20α-pregnanediol is described in A. Astier et al, *Bull. Soc. Chim.* No. 9-10, pp. 1581-1582 (1976); and other 14β-amino pregnanes and 14β-amino androstanes are described in A. Astier et al, *Tetrahedron*, Vol. 34, pp. 1481-1486 (1978). However, neither the pharmacological properties thereof nor their use in therapy has been described.

Amino derivatives of steroids which are useful in therapy, as described in French Patent Applications 2,494,697 and 2,494,698, include 3(5α)-amino 17α,20-pregnanediol, 3(5α)-amino 19-nor 20-pregnanol and amino derivatives. These compounds are taught to possess immunotherapeutic properties enabling them to be used as medication for the treatment of auto-immune disorders resulting from a deficiency in certain lymphocytes.

As a result of work undertaken by the present inventors, it has been surprisingly determined that new amino steroid derivatives, and in particular derivatives of the 20-pregnanol and 21-nor 20-pregnanol series, substituted at the 14-position by an amino group and at the 3-position by a sugar residue, and possibly containing an additional hydroxyl group at the 12-position, possess positive inotropic properties as well as supraventricular anti-arrhythmic properties.

SUMMARY OF THE INVENTION

An object of the present invention therefore is to provide a 14-amino steroid derivative substituted at the 3-position by a sugar derivative as well as their addition salts with mineral or organic acids.

A further object of the present invention is to provide a process for the preparation of 14-amino steroids substituted at the 3-position by a sugar derivative, from a 3,20-dihydroxy 14-amino steroid, or a 3,12,20-trihydroxy 14-amino steroid.

A still further object of the present invention is to provide a method of use of the above-described steroid derivatives, in human and veterinary medicine, as cardiotonic medication for the treatment of cardiac incapacity, as well as pharmaceutical compositions containing as an active ingredient at least one 14-amino steroid derivative, or a pharmaceutically acceptable salt thereof, and at least one carrier or diluent.

The above objects have been met by 14-amino steroid derivatives represented by general formula (I):

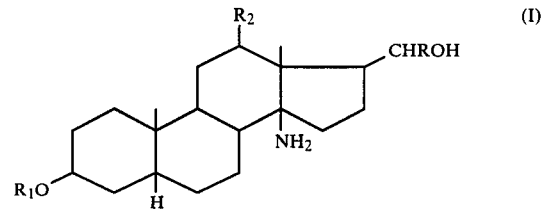

wherein R represents a hydrogen atom or a lower alkyl group having 1 to 4 carbon atoms, $R_1$ represents a substituted or unsubstituted sugar residue, and $R_2$ represents a hydrogen atom, a hydroxyl group, or an $-OR_3$ group, wherein $R_3$ is a substituted or unsubstituted sugar residue.

DETAILED DESCRIPTION OF THE INVENTION

As stated above, the present invention relates to 14-amino steroid derivatives represented by general formula (I):

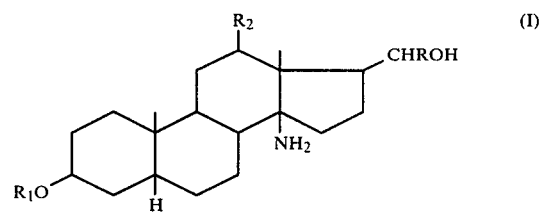

wherein R represents a hydrogen atom or a lower alkyl group having 1 to 4 carbon atoms, $R_1$ represents a substituted or unsubstituted sugar residue, and $R_2$ represents a hydrogen atom, a hydroxyl group, or an $-OR_3$ group, wherein $R_3$ is a substituted or unsubstituted sugar residue.

The 14-amino steroid derivatives of general formula (I) contain in their molecule several asymmetrical carbon atoms, in particular carbons at the 3-, 5-, 14-, 17- and 21-positions, as well as the carbon at the 12-position when $R_2$ is not a hydrogen atom. Thus, the derivatives can exist in various stereoisomeric forms. The present invention relates to the new products of general formula (I) in the form of either separated or mixed isomers.

The present invention also relates to the salts of the 14-amino steroids of general formula (I), and in particular to the salts obtained by the action of a mineral or organic acid, in accordance with conventional methods of the art. The acid used can be selected from among hydrochloric acid, oxalic acid, tartaric acid, fumaric acid, lactic acid, phosphoric acid, p-toluene sulfonic acid, formic acid, hydrobromic acid, maleic acid, sulfamic acid, etc.

In general formula (I) above, R preferably represents a hydrogen atom or a methyl group.

The sugar residue represented by $R_1$ in general formula (I) can be a substituted or unsubstituted monosaccharide residue, a substituted or unsubstituted oligosaccharide residue or a substituted or unsubstituted polysaccharide residue. For example, $R_1$ can be pentose or hexose modified or substituted as necessary, in order, for example, to form 2-deoxy or 6-deoxy hexose, 2,6-dideoxy hexose, 2-deoxy 2-amino hexose, 3-deoxy 3-amino hexose, 3-deoxy 3-methoxy hexose, 2,3,6- trideoxy hexose, 4,6-dideoxy 4-methoxy hexose, 2,3,6-trideoxy 2,3-didehydro hexose, etc.

Examples of monosaccharides which may be used in the present invention include glucose, rhamnose, fructose, galactose, mannose, arabinose, digitoxose, cymarose, xylose, lyxose, ribose, digitalose, 6-deoxy glucose, glucosamine, 4-amino 2,4,6-trideoxy lyxohexopyranose, 4-amino 4,6-dideoxy glycopyranose, 2,3-dideoxy rhamnopyranose, 4-methoxy 4,6-dideoxy rhamnopyranose, etc., and preferably the $\beta$-D or $\alpha$-L anomers thereof.

Disaccharides, such as saccharose, maltose or lactose or even various polysaccharides containing several sugars, may also be used in the present invention.

Among the compounds of general formula (I) above, the present invention preferably relates to those for which the sugar residue represented by $R_1$ is a glucose, rhamnose, galactose, fucose or digitoxose residue.

As indicated above, the 14-amino steroid derivatives of the present invention can exist in various stereoisomeric forms resulting from the presence of several asymmetrical carbon atoms in the steroid skeleton. The invention preferably relates to the derivatives of general formula (I) wherein the —$OR_1$ substituent at the 3-position, the hydrogen atom at the 5-position, the $R_2$ group at the 12-position, the —$NH_2$ group at the 14-position and the —CHROH substituent at the 17-position have the $\beta$ configuration. This configuration is not limitative and, for example, the hydrogen atom at the 5-position may be in the $\alpha$ configuration. In addition, the —OH group at the 20-position may have either the $\alpha$ or $\beta$ configurations when R is an alkyl group.

The present invention relates in particular to the 14-amino steroid derivatives constituted by 3-O-($\alpha$-L-rhamnopyranosyl) 14$\beta$-amino 21-nor 5$\beta$-pregnane 3$\beta$,20,-diol, 3-O-($\alpha$-L-rhamnopyranosyl) 14$\beta$-amino 5$\beta$-pregnane 3$\beta$,20$\alpha$-diol and its 20$\beta$ isomer, 3-O-($\beta$-D-digitoxosyl) 14$\beta$-amino 5$\beta$-pregnane 3$\beta$,20$\alpha$-diol, 3-O-(4-amino 2,3,6-trideoxy $\alpha$-L-lyxohexopyranosyl) 14$\beta$-amino 5$\beta$-pregnane 3$\beta$,20$\alpha$-diol, 3-O-($\alpha$-L-rhamnopyranosyl) 14$\beta$-amino 21-nor 5$\beta$-pregnane 3$\beta$,12$\beta$,20-triol, 3-O-($\alpha$-L-rhamnopyranosyl) 14$\beta$-amino 5$\beta$-pregnane 3$\beta$,12$\beta$,20$\beta$-triol and its 20$\alpha$ isomer, 3-O-($\beta$-D-digitoxosyl) 14$\beta$-amino 5$\beta$-pregnane 3$\beta$,12$\beta$,20$\beta$-triol and its 20$\alpha$, isomer and 3,12-di-O-($\alpha$-L-rhamnopyranosyl) 14$\beta$-amino 5$\beta$-pregnane 3$\beta$,12$\beta$,20$\beta$-triol.

The 14-amino steroid derivatives of general formula (I) can be prepared from 14-amino steroids represented by general formula (II) below:

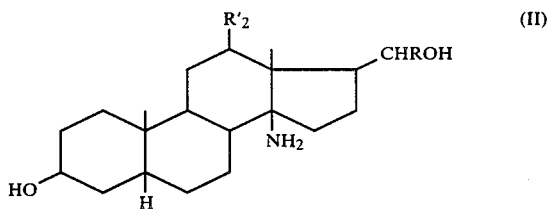

wherein R is a hydrogen atom or a lower alkyl group, preferably a methyl group, and $R'_2$ is a hydrogen atom or a hydroxyl group,
by carrying out the following steps:

(1) protecting the —$NH_2$ group at the 14-position and the —OH group at the 20-position, as well as, when necessary, the —OH group at the 12-position represented by $R'_2$; then (2) carrying out a coupling reaction with an activated sugar of the formula $R_1$—X wherein $R_1$ is defined as above and X represents a halogen atom or an acetyl group; and (3) eliminating, as necessary, the protective groups.

The activated sugars can for example be tri-O-acetyl digitoxose, tri-O-acetal, $\alpha$-L-rhamnosyl bromide, acetyl 3-O-benzoyl 2,4,6-trideoxy 4-trifluoroacetamido $\alpha,\beta$-L-lyxohexopyranoside, 2,3-di-O-acetyl 4,6-dideoxy 4-trifluoroacetamido glycopyranosyl bromide, tetra-O-acetyl $\alpha$-D-glycosyl bromide, etc.

The protection of the —$NH_2$ group at the 14-position and of the —OH group at the 20-position is carried out by conventional techniques, for example the —$NH_2$ group can be transformed into a —$NHCOCF_3$ trifluoroacetamido group by the action of anhydrous trifluoroacetic acid in the presence of triethylamine, or into a formamido group by the action of anhydrous acetic acid in formic acid. The —OH group can be acetylated by the action of anhydrous acetic acid in a suitable solvent such as pyridine.

The functional groups of the sugar derivatives are preferably protected before carrying out the coupling reaction with the 14-amino steroid. The hydroxyl groups of the sugar derivatives can be protected by conventional methods, in particular by acylation or by benzoylation. For example, the hydroxyl groups of a digitoxose or a rhamnose can be transformed into acetoxy groups by acetylation by means of anhydrous acetic acid such as described in E. Fisher et al, *Chem. Ber.* No. 53, pp. 2362 (1920). The amino groups, which may be present in the sugar derivative are also protected in advance by an acyl group, and preferably by an a trifluoroacetyl group.

The protective groups are then eliminated, after the coupling between the sugar derivative and the 14-amino steroid, in accordance with conventional techniques, for example by heating in a base medium.

The coupling reaction is carried out by reacting the previously protected sugar derivative at the level of its anomeric carbon atom with the hydroxy group at the 3-position of the 14-amino steroid on which protective groups have been introduced at the level of the substituents at the 14- and 20-positions, in a suitable organic solvent. Generally an equivalent of the sugar derivative is used, but it may also be used in excess, for example between 1.5 and 2.5 moles of sugar derivative may be used for 1.0 mole of the 14-amino steroid.

The operating conditions may be selected from among conventional methods, for example when using an amino sugar, the coupling methods described in D. M. von Niekerk et al, *Experientia* No. 28, p. 123 (1972), or W. Meyer et al, *Chem. Ber.* No. 104, p. 1 (1971) can be used. When a sugar such as 2,6-dideoxy hexose or 4-amino 2,4,6-trideoxy hexose is used, it is preferably to carry out coupling using the method described in J. Boivin, C. Monneret and M. Pais, *Tetrahedron Letters,* p. 1111 (1980).

The coupling reaction may be carried out in accordance with the above techniques in at least one solvent such as benzene or toluene, acetonitrile, methylene chloride, or dioxane, at room temperature. It may be useful to heat the reactive medium to activate the reaction depending upon the reactants used.

The coupling reaction is preferably carried out with the hydroxyl group at the 3-position of the 14-amino steroid protected at the 14-position and at the 20-position but not protected at the 12-position, since the reactivity of the hydroxyl group at the 3-position is greater than that of the hydroxyl group present at the 12-position. The sugar derivative at the 3-position and at the 12-position which is formed as a secondary product during the coupling reaction is easily separated. In order to form the sugar derivative at the 3-position and at the 12-position in a predominant manner, the sugar derivative may be used in excess.

The 14-amino steroids of general formula (II) used as starting materials, where $R'_2$ is a hydrogen atom, can be prepared as described in French Patent Application No. 82.14038, by reduction and then acetylation of a 3,14-dihydroxy steroid with a —COR acyl group at the 17-position, wherein R is a hydrogen atom or an alkyl group, to form a 3,14,20-trihydroxy steroid which is O-acetylated at the 3- and 20-positions, which is treated with a boron triazoictrifluoride acid complex before carrying out reduction with a metallic hydride or by catalytic hydrogenation. Similarly, the 14-amino steroids of general formula (II) where $R'_2$ is a hydroxyl group, can be prepared by the same process, starting with a 3,12,20-trihydroxy steroid, as indicated in French Patent Application No. 83.10031.

For example, the 14β-amino 5β-pregnane 3β,20α-diol represented by formula (II) where R is a methyl group, and $R'_2$ is a hydrogen atom, can be obtained from 20-oxo 5β-pregnane 3β,14β-diol on which reduction with potassium borohydride is carried out, then acetylation with anhydrous acetic acid in pyridine to form 3,20-di-O-acetyl 5β-pregnane 3β,14β,20β-triol which is treated with triazoic acid in the presence of boron trifluoride etherate in order to carry out reduction with a mixed lithium and aluminum hydride. The method described in Astier et al, Tetrahedron No. 34, p. 1481–1486 (1978) can also be used.

As indicated above, the 14-amino steroid derivatives represented by general formula (I) possess interesting pharmacological properties, in particular positive inotropic properties and supraventricular anti-arrhythmic properties which will be described in more detail below and which enable their use in human and veterinary medicine for the treatment of cardiac incapacity.

The following examples illustrate the invention and are in no way intended to limit the scope thereof.

EXAMPLE 1

3-O-(β-D-digitoxosyl) 14β-amino 21-nor 5β-pregnane 3β,20-diol 1 ml of anhydrous acetic acid was added under agitation to a solution of 3.2 g of 14β-amino 21-nor 5β-pregnane 3β,20-diol in 40 ml of pyridine cooled to 0° C.

After 30 minutes of agitation at 0° C., a solution of ice-cold sodium bicarbonate was added to the reactive medium, the agitation was continued for an additional 10 minutes, and then the solution was extracted with methylene chloride and evaporated until dry.

By crystallization of the residue (3.62 g) in a benzene/hexane mixture, 3.0 g of 20-O-acetyl 14β-amino 21-nor 5β-pregnane 3β,20-diol was obtained (yield 83%).

To a solution of 3.66 g of the above derivative in 100 ml of anhydrous methylene chloride cooled to 0° C., 3.4 ml of triethylamine and 3.1 ml of anhydrous trifluoroacetic acid were added under magnetic agitation. Agitation was continued for an additional 20 minutes allowing a return to room temperature and then was evaporated until dry. The residue was again dissolved in methylene chloride and the solution obtained was washed with a saturated solution of sodium bicarbonate, then with water, and finally dried in the usual manner and evaporated until dry. The product obtained was dissolved in 600 ml of methanol, then passed slowly over a period of 5 hours on a column of 300 ml of IR 45 resin (OH phase). The column was washed with 300 ml of methanol. The collected solutions, evaporated until dry, yielded 4.52 g of pure 20-O-acetyl 14β-trifluoroacetamido 21-nor 5β-pregnane 3β,20-diol in thin layer chromatography, which did not crystallize.

35 g of dry p-toluene sulfonic acid was added to a solution of 0.33 g of the above derivative and 0.40 g of tri-O-acetyl digitoxose in 30 ml of benzene. After 1 hour of agitation at room temperature, a solution of saturated sodium bicarbonate was added to the reactive medium, and the mixture was then extracted with methylene chloride. The residue (0.6 g) was chromatographed on Merck H60 silica (eluent hexane/AcOEt 75/25). This yielded 0.4 g of a mixture of 3-O-(3,4-di-O-acetyl α and β-D-digitoxosyl) 20-O-acetyl 14β-trifluoroacetamido 21-nor 5β-pregnane 3β,20-diol.

To a solution of this mixture in 16 ml of methanol, 4 ml of 5N sodium hydroxide was added under agitation and the solution was heated at reflux for 2 hours and 30 minutes. After this time, the solution was diluted with water and extracted with methylene chloride. The product obtained (0.27 g) was chromatographed on Merck H60 silica (eluent $CH_2Cl_2$/MeOH/$NH_4OH$ 93/7/0.4). In this manner 0.15 g of the β-D derivative was obtained which crystallized in the methanol ether mixture, as well as 0.11 g of the α-D anomer, which crystallized in the same mixture of solvents.

Melting point: F=198°–199° C. (β-D anomer), 226° C. (α-D anomer).

$/\alpha_D/ = -31°$ (c=1, $CHCl_3$)

NMR spectrum ($CDCl_3$) $\delta = 0.93$ ($CH_3$-19) 0.98 ($CH_3$-18) 1.30 ($CH_3$-6') 4.87 (H-1') ppm (β-D anomer); $\delta = 0.95$ ($CH_3$-19) 1.00 ($CH_3$-18) 1.31 ($CH_3$-6') 4.99 (H-1') ppm (α-D anomer).

EXAMPLE 2

3-O-(α-L-rhamnopyranosyl) 14β-amino 21-nor 5β-pregnane 3β,20-diol 4.96 g of mercuric cyanide was added to a solution containing 4.6 g of 20-acetyl 14β-trifluoroacetamido 21-nor 5β-pregnane 3β,20-diol obtained as indicated in Example 1 and 6.95 g of 2,3,4-tri-O-acetyl α-L-rhamnosyl bromide in 235 ml of acetonitrile. After 1 hour of agitation at room temperature, the solution was diluted with methylene chloride and extracted by washing with a saturated solution of sodium hydrogenocarbonate. The raw product obtained (7.82 g) was chromatographed on Merck H60 silica (eluent $CH_2CL_2$/MeOH 0.3%).

5.36 g of pure 3β-O-(2,3,4-tri-O-acetyl α-L-rhamnopyranosyl)-3β 20-O-acetyl 14β-trifluoroacetamido 21-nor 5β-pregnane 3β,20-diol was obtained which did not crystallize.

To 4.6 g of the above derivative in solution in 130 ml of methanol, 32 ml of 5N sodium hydroxide were added and this was heated at reflux for 4 hours. The solution was then diluted with methylene chloride and washed with water and then with a solution of semi-saturaated sodium chloride (maintaining a sufficient concentration of methanol). 3 g of pure product was obtained in thin layer chromatography, which crystallized in the methanol/ether mixture.

Melting point: F=244° C.

/α_D/ = −53° (c=1, CHCL_3/MeOH 80/20)

NMR spectrum (CDCl_3) δ=0.90 (CH_3-19) 0.95 (CH_3-18) 1.20 (CH_3-6') 4.82 (H-1') ppm

EXAMPLE 3

3-O-(4-amino 4,6-dideoxy β-D-glucopyranosyl) 14β-amino 21-nor 5β-pregnane 3β,20-diol 0.35 g of mercuric cyanide and 0.24 g of mercuric bromide were added to an aromatic solution containing 0.6 g of 20-O-acetyl 14β-trifluoroacetamido 21-nor 5β-pregnane 3β,20-diol obtained as indicated in Example 1. This was brought to reflux and 0.27 g of 2,3-diacetyl 4,6-dideoxy 4-trifluoroacetamido glucopyranosyl bromide in solution in 6 ml of benzene was added thereto. After 1 hour of boiling at reflux, the same quantity of bromosugar (0.27 g in 6 ml of benzene) was added and after another hour an additional 0.27 g of bromosugar in 4 ml of benzene was added. This was allowed to reflux for 2.5 hours, then cooled, diluted with methylene chloride and extracted by washing with a saturated solution of sodium bicarbonate. The evaporated organic solvent left a residue (1.05 g) which was chromatographed on Merck H60 silica (eluent CH_2Cl_2/MeOH 0.4%). This yielded 0.46 g of pure product in TLC, which crystallized in an acetone-hexane mixture.

3.5 ml of 5N sodium hydroxide was added to a solution of 0.35 g of the above product in 14 ml of methanol and heated at reflux for 3 hours. The solution was then diluted with water and extracted with methylene chloride. This yielded 0.18 g of product which crystallized in an ethanol-ether mixture.

Melting point: F=233° C.

/α_D/ = −34° (c=1, CHCl_3)

EXAMPLE 4

3-O-(4-amino 2,4,6-trideoxy α-L-lyxohexopyranosyl) 14β-amino 21-nor 5β-pregnane 3β,20-diol 24 ml of anhydrous acetic acid at room temperature was added to a solution of 1.8 g of 14β-amino 21-nor 5β-pregnane 3β,20-diol described in Example 6 of French Pat. No. 2,464,270 in 39.6 ml of formic acid. The temperature of the medium was brought to 60° C. for 30 minutes, then to 100° C. Then 8 ml of anhydrous acetic acid were added and this was allowed to react for approximately one hour at the same temperature.

After cooling and dilution with water, the solution was extracted with dichloromethane, washed with bicarbonated water, dried on sodium sulfate and vacuum evaporated until dry.

2.17 g of a mixture of two neutral products were formed, to which 42 ml of 0.25N ethanol sodium hydroxide cooled to +5° C. was added. After one hour at room temperature, the solution was diluted with water, extracted with methylene chloride and, after washing, 2.28 g of a residue in foam form (rough quantitative yield) was obtained.

A solution of 2.18 g of the above product in 12 ml of pyridine was cooled to −15° C. by means of an ice-salt bath. 0.55 g of anhydrous acetic acid was added thereto and the solution was allowed to rise to room temperature without removing the bath, over a two hour period. Next, two additions, each of 0.16 g of anhydrous acetic acid, were carried out, at −15° C., allowing the temperature to rise to room temperature between each addition. Then, 120 ml of water was added and the solution was extracted with benzene and washed with a 5% aqueous solution of citric acid and then with water.

The raw product thus obtained was chromatographed on a silica column; a dichloromethane/methanol (98/2) mixture was used as an eluent; in order to separate, after crystallization in a benzene/isopropyl ether mixture, 1.23 g of 20-acetyl 14β-formylamino 21-nor 5β-pregnane 3β,20-diol (yield 60%).

0.5 g of dry p-toluene sulfonic acid was added to a solution of 0.60 g of the above product and 1.16 g of acetyl 3-O-benzoyl 2,4,6-trideoxy 4-trifluoroacetamido α,β-L-lyxohexopyranoside in 80 ml of a mixture of equal parts of benzene and methylene chloride. The solution was left under agitation at room temperature for 3 hours and then a saturated aqueous solution of sodium bicarbonate was added thereto and the solution was extracted with methylene chloride. The raw product obtained (1.66 g) was chromatographed on 50 g of Merck H60 silica (eluent: hexane/acetone 3/1) and yielded 0.84 g of a mixture of α and β-L anomers. By crystallization in an acetone/hexane mixture, the pure α-L anomer was separated, which was 0.50 g.

The α-L anomer was placed in solution in 24 ml of methanol, 6 ml of 5N sodium hydroxide was added and the mixture was heated at reflux for one hour. Then, the solution was diluted with water and extracted with chloroform. In this manner the protective groups were eliminated and 0.36 g of the desired product was obtained, which crystallized in a methanol/ether mixture.

Melting point: F=219°-220° C.

/α_D/ = −91° (c=1, CHCl_3)

NMR spectrum (CDCl_3) δ=0.93 (CH_3-19) 1.00 (CH_3-18) 1.17 (CH_3-6') 4.91 (H-1') ppm.

EXAMPLE 5

3-O-(β-D-digitoxosyl) 14β-amino 5β-pregnane 3β,20α-diol

Using the process described in Example 1, 1.7 g of 14β-amino 5β-pregnane 3β,20α-diol was treated with anhydrous acetic acid, then the product obtained (non-crystallized) was reacted with anhydrous trifluoroacetic acid to form 2.4 g of 20-O-acetyl 14β-trifluoroacetamido 5β-pregnane 3β,20α-diol which crystallized in an ether/hexane mixture.

By proceeding as in Example 1, 1.1 g of tri-O-acetyl digitoxose were reacted with 0.9 g of the above product in 120 ml of benzene in the presence of 0.8 g of dry p-toluene sulfonic acid.

After washing, extraction, treatment with sodium hydroxide by heating at reflux, and then purification, 0.35 g of the β-D anomer was obtained as well as 0.26 g of the α-D anomer which both crystallized in a methanol/diethyl ether mixture.

Melting point: F=208° C. (β-D anomer)

/α_D/ = −26° (c=1.5 CHCl_3)

EXAMPLE 6

3-O-(α-L-rhamnopyranosyl) 14β-amino 5β-pregnane 3β,20α-diol

The method used in Example 5 was used, however, tri-O-acetyl digitoxose was replaced with 2,3,4-tri-O-acetyl α-L-rhamnosyl bromide in acetonitrile, in the presence of mercuric cyanide.

After reaction for one hour at room temperature, dilution in methylene chloride and washing with a saturated solution of sodium bicarbonate, 3β-O-(2,3,4-tri-O-acetyl α-L-rhamnopyranosyl) 20-O-acetyl 14β-trifluoroacetamido 5β-pregnane 3β,20α-diol was obtained which was purified by chromatography on a silica column.

The above product, in solution in methanol, was added to 5N sodium hydroxide and heated at reflux for 8 hours. After dilution with water and extraction with methylene chloride, 3-O-(α-L-rhamnopyranosyl) 14β-amino 5β-pregnane 3β,20α-diol was obtained which crystallized in an ethanol/diethyl ether mixture.

Melting point: F=265° C.
/α$_D$/ = −49° (c=0.8 CHCl$_3$/MeOH 80/20)
NMR spectrum (CDCl$_3$+CD$_4$O) δ=0.96 (CH$_3$-19) 1.00 (CH$_3$-18) 1.06 (CH$_3$-21) 1.28 (CH$_3$-6′) 4.90 (H-1′) ppm.

EXAMPLE 7

3-O-(α-L-rhamnopyranosyl) 14β-amino 5β-pregnane 3β,20β-diol

Using the process of Example 1, 20-acetoxy 14β-trifluoroacetamido 5β-pregnane 3β,20β-diol was prepared by the action of anhydrous acetic acid and then anhydrous trifluoroacetic acid on 14β-amino 5β-pregnane 3β,20β-diol.

The product obtained was reacted with 2,3,4-tri-O-acetyl α-L-rhamnosyl bromide in acetonitrile in the presence of mercuric cyanide, using the coupling method described in Example 2. After treatment with sodium hydroxide in methanol and by heating at reflux, 3-O-(α-L-rhamnopyranosyl) 14β-amino 5β-pregnane 3β,20β-diol was obtained which crystallized in ethanol.

Melting point: F=263°-264° C.
/α$_D$/ = −52° (c=0.7 CHCl$_3$/MeOH 80/20)
NMR spectrum (CDCl$_3$+CD$_4$O) δ=0.95 (CH$_3$-19) 1.16 (CH$_3$-18) 1.30 (CH$_3$-21) 1.30 (CH$_3$-6′) 4.83 (H-1′) ppm.

EXAMPLE 8

3-O-(α-L-rhamnopyranosyl) 14β-amino 3β,20α-pregnanediol

The process of Example 6 was repeated, however, 14β-amino 5β-pregnane 3β,20α-diol was replaced with the 14β-amino 3β,20α-pregnanediol isomer whose proton at the 5-position has the 5α configuration, and by carrying out the coupling with 2,3,4-tri-O-acetyl α-L-rhamnosyl bromide under the same conditions.

After treatment with sodium hydroxide in solution in methanol, and by heating at reflux 3β-O-(α-L-rhamnopyranosyl) 14β-amino 20α-pregnanol was obtained which crystallized in an ethanol/ether mixture.

Melting point: F=271° C.
NMR spectrum (CDCl$_3$+CD$_4$O) δ=0.78 (CH$_3$-19) 0.98 (CH$_3$-18) 1.03 (CH$_3$-21) 1.25 (CH$_3$-6′) 4.76 (H-1′) ppm.

EXAMPLE 9

3-O-(4-amino 2,4,6-trideoxy α-L-lyxohexopyranosyl) 14β-amino 5β-pregnane 3β,20α-diol The process of Example 4 was repeated, however, 14β-amino 21-nor 5β-pregnane 3β,20-diol was replaced with 14β-amino 5β-pregnane 3β,20α-diol to obtain the desired product which crystallized in a methanol/ethyl ether mixture.

Melting point: F=224° C.
/α$_D$/ = −79° (c=1, CHCl$_3$)

EXAMPLE 10

3-O-(α-L-rhamnopyranosyl) 14β-amino 5β-pregnane 3β,12β,20β-triol 1 ml of anhydrous acetic acid was added to a solution of 50 ml of pyridine cooled to 0° C. and containing 3.5 g of 14β-amino 5β-pregnane 3β,12β,20β-triol. The reaction medium was maintained under agitation. It was allowed to react for approximately 30 minutes at 0° C. under agitation, then a solution of ice-cold sodium bicarbonate was added. After 10 minutes, it was extracted with methylene chloride and the solvent was eliminated by evaporation.

In this manner 3.7 g of 20-O-acetyl 14β-amino 5β-pregnane 3β,12β,20β-triol was obtained which could be purified by crystallization.

The above product was dissolved in 100 ml of methylene chloride at 0° C., then 3.5 ml of triethylamine and 3.1 ml of anhydrous trifluoroacetic acid were added. The reaction mixture was maintained under agitation for approximately 20 minutes and then the solvent was eliminated by evaporation.

The residue obtained was purified by redissolving it in methylene chloride, then washing with a solution of sodium bicarbonate using conventional techniques. After dissolving the residue in methanol and passage on an IR 45 resin column, 4.6 g of 20-O-acetyl 14β-trifluoroacetamido 5β-pregnane 3β,12β,20β-triol was obtained.

1.9 g of mercuric cyanide was added to a solution of 3 g of the derivative obtained as indicated above and 2.7 g of 2,3,4-tri-O-acetyl L-rhamnosyl bromide in 160 ml of acetonitrile. After 1 hour of agitation at room temperature, the solution was diluted with methylene chloride and extracted by washing with a saturated solution of sodium bicarbonate. After chromatography on Merck H60 silica, using a methylene chloride-methanol mixture (98.5/1.5) as the eluent, 3 g of 3-O-(2,3,4-tri-O-acetyl α-L-rhamnopyranosyl) 20-O-acetyl 14β-trifluoroacetamido 5β-pregnane 3β,12β,20β-triol was obtained.

The product thus obtained was dissolved in 60 ml of methanol and 6 ml of 10N sodium hydroxide was added thereto. The solution was heated at reflux for 6 hours, then diluted with water and extracted with methylene chloride. In this manner 1 g of raw 3-O-(α-L-rhamnopyranosyl) 14β-amino 5β-pregnane 3β,12β,20β-triol was obtained, which was purified by chromatography on Merck H60 silica using a methylene chloride-methanol-ammonia mixture (80/20/2) as the eluent.

The corresponding hydrochloride was prepared by action of concentrated hydrochloric acid in a methanol solution. The product formed was filtered, dissolved in isopropanol and precipitated with ether.

Melting point: F=260° C.
NMR spectrum (CDCL$_3$/CD$_3$OD 4/1) δ=0.93(s, Me19) 1.06(s, Me18) 1.26(d,j=7,Me21) 1.27(d,j=6,Me6′) 3.28(m, H12) 4.78(m, H1′) ppm

EXAMPLE 11

3,12-di-O-(α-L-rhamnopyranosyl) 14β-amino 5β-pregnane 3β,12β,20β-triol 3.2 g of mercuric cyanide was added to a solution of 3.0 g of 20-O-acetyl 14β-trifluoroacetamido 5β-pregnane 3β,12β,20β-triol obtained as indicated in Example 10 and 4.4 g of 2,3,4-tri-O-acetyl L-rhamnosyl bromide in 160 ml of acetonitrile.

The solution was allowed to react for 1 hour under agitation at room temperature. It was diluted with methylene chloride and extracted by washing with a saturated solution of sodium carbonate. The product obtained was dissolved in 100 ml of methanol and 10 ml of 10N sodium hydroxide was added. The solution was heated at reflux for approximately 6 hours, the solvent was evaporated and 50 ml of water were added. A precipitate was formed which was filtered off and dissolved in a mixture of methylene chloride and methanol (90/10).

After extraction, drying and evaporation using conventional techniques, 3.1 g of the desired product was obtained which were purified by crystallization in absolute ethanol.

Melting point: F=240° C.

IR spectrum (Nujol) $\nu=3440, 3370, 3260, 1620, 1590$ cm$^{-1}$

EXAMPLE 12

Positive Inotrophic Activity

Experiments carried out on the 14-amino steroid derivatives represented by general formula (I) have in particular shown positive inotropic activity as well as supraventricular antiarrhythmic properties.

More particularly, the derivatives in accordance with the present invention possess positive inotropic activity greater than or equal to that of well-known reference compounds such as ouabain and digoxin.

Inotropic activity has been verified on the isolated guinea pig auricle under normal experimental conditions, by recording the range of contractions for various doses administered in relation to control values.

Table 1 below demonstrates the increase in the force of contraction as a function of concentration for digoxin (comparitive compound) and for the products of the invention described in Examples 6 and 7.

TABLE 1

| | Range of contractions in relation to the control values | | | | |
|---|---|---|---|---|---|
| | Concentration (Moles/l) | | | | |
| Compound | $2 \times 10^{-7}$ | $10^{-6}$ | $2 \times 10^{-6}$ | $6 \times 10^{-6}$ | $10^{-5}$ |
| Digoxin | +38% | +100% | +114% | +128% | +128% |
| Ex. No. 6 | — | +43% | +63% | +143% | +148% |
| Ex. No. 7 | +50% | +97% | +178% | +233% | +206% |

These results show that the products in accordance with the present invention cause increases in the force of contraction which are considerably greater than those caused by digoxin, at various concentrations.

EXAMPLE 13

Inhibition of Membraneous ATPase

The 14-amino steroid derivatives of the present invention also have a capacity for inhibition of membraneous ATPase which is molecularly greater than or equal to that of digoxin or ouabain.

The results obtained using the derivatives of the invention described in Examples 2, 6 and 7 and ouabain and digoxin are shown in Table 2 below.

In Table 2, the ED50 value is the dose causing 50% inhibition of membraneous ATPase.

TABLE 2

| | ED50 |
|---|---|
| ouabain | $3.6 \times 10^{-9}$M |
| digoxin | $5.3 \times 10^{-9}$M |
| Ex. No. 2 | $1.3 \times 10^{-10}$M |

TABLE 2-continued

| | ED50 |
|---|---|
| Ex. No. 6 | $1.8 \times 10^{-10}$M |
| Ex. No. 7 | $7.0 \times 10^{-11}$M |

EXAMPLE 14

Toxicity

The derivatives of the present invention are distinguished from known substances of the digitalic series, such as digoxin and ouabain, by advantageous modification of their toxic activity.

For example, the derivatives of the present invention described in Example 6 provides, in an anesthetized dog, without any signs of toxicity, a 150% increase in cardiac contractility, whereas, under the same experimental conditions, toxic signs appear for digoxin when cardiac contractility is increased by only approximately 50%. Similarly, the toxicity of the derivatives of the invention is reversible, that is, stopping their administration is sufficient to make problems observed using an electrocardiogram disappear.

These results show that the derivatives of the invention can be used in human and veterinary medicine, in particular as medication for the treatment of cardiac incapacity.

EXAMPLE 15

Methods of Administration

The derivatives of general formula (I) and their pharmaceutically acceptable salts can be administered in conventional forms, the active ingredient being diluted in an appropriately selected pharmaceutically acceptable carrier or diluent, for example, in the form of tablets, capsules, lozenges, suppositories, injectable solutions or syrups.

By way of example, tablets can be prepared by mixing the derivative of general formula (I) or one of its salts, with one or several solid diluents, such as lactose, mannitol, starch, polyvinylpyrrolidone, magnesium stearate, talc, etc. When desired, the tablets may comprise several layers superposed around a nucleus, in accordance with conventional techniques, in order to ensure progressive release or a delayed effect of the active ingredient. The coating may be composed of, for example, one or several layers of polyvinyl acetate, carboxymethylcellulose or cellulose acetophthalate.

Tablets corresponding to the following formulae have been prepared:

| Tablet A: | |
|---|---|
| 3-0-(α-L-rhamnopyranosyl) 14β-amino 5β-pregnane 3β,12β, 20β-triol (hydrochloride) | 0.2 mg |
| excipient | 100 mg |
| (excipient: starch, talc, lactose, magnesium stearate). | |
| Tablet B: | |
| 3-(α-L-rhamnopyranosyl) 14β-amino 5β-pregnane 3β, 20β-diol | 3 mg |
| excipient | 100 mg |
| (excipient: starch, talc, lactose, magnesium stearate). | |

The derivatives of the invention may also be administered in the form of a syrup or drinkable solution obtained by dissolving the derivative of formula (I) or one of its pharmaceutically acceptable salts, in water or glycerol, for example, and by adding, as necessary, a conventional additive such as a sweetener and an antioxidant.

Injectable solutions can be prepared using well-known techniques and can comprise, for example, a solution containing a derivative of formula (I) or one of its pharmaceutically acceptable salts, dissolved in double distilled water, a hydroalcoholic solution, propylene glycol, etc., or a mixture of such solvents. Where necessary, an appropriate additive such as a preservative may be added.

Doses administered are determined by the physician dependent upon the means of administration selected, the degree of the condition being treated, the length of treatment, etc. By way of example, in the case of oral administration in man, doses can be between 0.05 and 2 mg/kg, for a derivative such as that of Example 2, 6 or 7. Where necessary, doses may be lower, for example, in the case of the derivative of Example 10, they are preferably between 0.001 and 0.05 mg/kg.

What is claimed is:

1. 14-amino steroid derivatives represented by general formula (I):

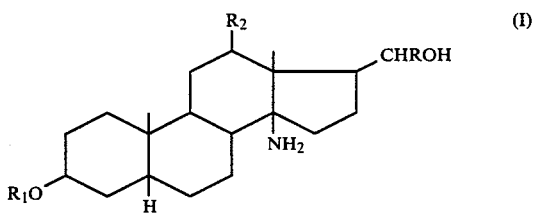

(I)

wherein R represents a hydrogen atom or a lower alkyl group having 1 to 4 carbon atoms, $R_1$ represents a substituted or unsubstituted sugar residue, and $R_2$ represents a hydrogen atom, a hydroxy group or an —$OR_3$ group, wherein $R_3$ is a substituted or unsubstituted sugar residue, and acid salts thereof.

2. The 14-amino steroid derivatives of claim 1, wherein R represents a hydrogen atom or a methyl group.

3. The 14-amino steroid derivatives of claim 1, wherein $R_1$ is a substituted or unsubstituted monosaccharide residue, and $R_2$ is a hydrogen atom or a hydroxyl group.

4. The 14-amino steroid derivatives of claim 3, wherein $R_1$ represents a modified or substituted or unsubstituted pentose or hexose residue.

5. The 14-amino steroid derivatives of claim 4, wherein $R_1$ represents a substituted or unsubstituted glucose residue, rhamnose residue, galactose residue, fucose residue or digitoxose residue.

6. The 14-amino steroid derivatives of claim 1, wherein said derivative is at least one member selected from the group consisting of 3-O-(α-L-rhamnopyranosyl) 14β-amino 21-nor 5β-pregnane, 3β,20-diol, 3-O-(α-L-rhamnopyranosyl) 14β-amino 5β-pregnane 3β,20α-diol and its 20β isomer, 3-O-(β-D-digitoxosyl) 14β-amino 5β-pregnane 3β,20α-diol, 3-O-(4-amino 2,3,6-trideoxy α-L-lyxohexopyranosyl) 14β-amino 5β-pregnane 3β,20α-diol, 3-O-(α-L-rhamnopyranosyl) 14β-amino 21-nor 5β-pregnane 3β,12β,20-triol, 3-O-(α-L-rhamnopyranosyl) 14β-amino 5β-pregnane 3β,12β,20β-triol and its 20α isomer, 3-O-(β-D-digitoxosyl) 14β-amino 5β-pregnane 3β,12β,20α-triol or 3,12-di-O-(α-L-rhamnopyranosyl) 14β-amino 5β-pregnane 3β,12β,20β-triol.

7. A process for the preparation of the 14-amino steroid derivatives of claim 1, comprising:

(1) protecting the —$NH_2$ group at the 14-position and the —OH group at the 20-position of the 14-amino steroid of general formula (II):

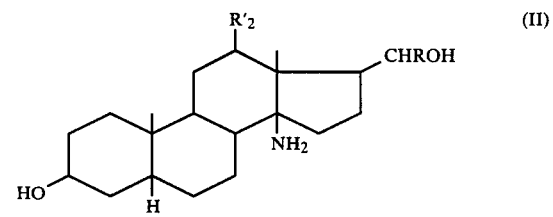

(II)

wherein R is a hydrogen atom or a lower alkyl group, and $R'_2$ is a hydrogen atom or a hydroxyl group;

(2) carrying out a coupling reaction with an activated sugar of the formula $R_1$—X, wherein $R_1$ is a sugar residue and X is a halogen atom or an acetylated group; and (3) if desired, removing the protective groups, wherein the —$NH_2$ group at the 14-position is protected by transformation into (a) a trifluoroacetamido group by the action of anhydrous trifluoroacetic acid in the presence of triethylamine, or (b) a formamido group by the action of anhydrous acetic acid in formic acid; and the —OH group at the 20-position is protected by acetylation by anhydrous acetic acid in pyridine.

8. The process of claim 7, wherein the sugar derivative of the formula $R_1$—X is added in excess.

9. Pharmaceutical compositions comprising a pharmaceutically acceptable amount of at least one 14-amino steroid derivative of claim 1 as an active ingredient and at least one pharmaceutically acceptable diluent or carrier.

10. Pharmaceutical compositions comprising a pharmaceutically acceptable amount of at least one 14-amino steroid derivative of claim 2 as an active ingredient and at least one pharmaceutically acceptable diluent or carrier.

11. Pharmaceutical compositions comprising a pharmaceutically acceptable amount of at least one 14-amino steroid derivative of claim 3 as an active ingredient and at least one pharmaceutically acceptable diluent or carrier.

12. Pharmaceutical compositions comprising a pharmaceutically acceptable amount of at least one 14-amino steroid derivative of claim 4 as an active ingredient and at least one pharmaceutically acceptable diluent or carrier.

13. Pharmaceutical compositions comprising a pharmaceutically acceptable amount of at least one 14-amino steroid derivative of claim 5 as an active ingredient and at least one pharmaceutically acceptable diluent or carrier.

14. Pharmaceutical compositions comprising a pharmaceutically acceptable amount of at least one 14-amino steroid derivative of claim 6 as an active ingredient and at least one pharmaceutically acceptable diluent or carrier.

15. The 14-amino steroid derivative of claim 2, wherein $R_1$ is a substituted or unsubstituted monosaccharide residue, and $R_2$ is a hydrogen atom or a hydroxyl group.

16. Pharmaceutical compositions comprising a pharmaceutically acceptable amount of at least one 14-amino steroid derivative of claim 15 as an active ingredient and at least one pharmaceutically acceptable diluent or carrier.

* * * * *